(12) United States Patent
Zhang et al.

(10) Patent No.: US 11,565,116 B2
(45) Date of Patent: Jan. 31, 2023

(54) INTERFERENTIAL STIMULATION METHOD AND SYSTEM FOR NEUROMODULATION

(71) Applicant: Boston Scientific Neuromodulation Corporation, Valencia, CA (US)

(72) Inventors: Tianhe Zhang, Studio City, CA (US); Joseph M. Bocek, Seattle, WA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 156 days.

(21) Appl. No.: 16/844,735

(22) Filed: Apr. 9, 2020

(65) Prior Publication Data
US 2020/0324119 A1 Oct. 15, 2020

Related U.S. Application Data

(60) Provisional application No. 62/831,999, filed on Apr. 10, 2019.

(51) Int. Cl.
*A61N 1/36* (2006.01)
*A61N 1/372* (2006.01)

(52) U.S. Cl.
CPC ..... *A61N 1/36167* (2013.01); *A61N 1/36185* (2013.01); *A61N 1/36196* (2013.01); *A61N 1/37247* (2013.01); *A61N 1/36164* (2013.01)

(58) Field of Classification Search
CPC ............ A61N 1/36167; A61N 1/36185; A61N 1/36196; A61N 1/37247; A61N 1/36164;
(Continued)

(56) References Cited

U.S. PATENT DOCUMENTS

| 5,324,317 A | 6/1994 | Reiss |
| 5,324,327 A | 6/1994 | Cohen |

(Continued)

OTHER PUBLICATIONS

Grossman, Nir, et al., "Noninvasive Deep Brain Stimulation via Temporally Interfering Electric Fields", Cell 169, 1029-1041, Jun. 1, 2017.

*Primary Examiner* — Eugene T Wu
(74) *Attorney, Agent, or Firm* — Schwegman Lundberg & Woessner, P.A.

(57) ABSTRACT

An example of a system for delivering neurostimulation energy may include a programming control circuit and a user interface. The programming control circuit may be configured to generate stimulation parameters according to a neurostimulation program including a pattern of interferential stimulation configured to effect asynchronous and/or non-regular activation of nerve fibers by simultaneously delivering a first stimulation current having a first waveform with a first frequency using a first electrode configuration and a second stimulation current having a second waveform with a second frequency using a second electrode configuration. The user interface may be configured to determine the neurostimulation program and to provide the pattern of interferential stimulation with modulation of the first waveform, the second waveform, the first electrode configuration, and/or the second electrode configuration to result in a time-varying beat frequency capable of effecting the asynchronous and/or non-regular activation of the nerve fibers.

20 Claims, 16 Drawing Sheets

(58) Field of Classification Search
CPC .............. A61N 1/36062; A61N 1/323; A61N 1/36171; A61N 1/0551
See application file for complete search history.

(56) References Cited

U.S. PATENT DOCUMENTS

| | | |
|---|---|---|
| 6,560,487 B1 | 5/2003 | Mcgraw et al. |
| 8,175,705 B2 | 5/2012 | Libbus |
| 8,977,363 B2 | 3/2015 | Carroll et al. |
| 9,320,902 B2 | 4/2016 | Carroll |
| 9,630,012 B2 | 4/2017 | Carroll |
| 10,576,282 B2 | 3/2020 | Doan et al. |
| 2012/0271395 A1* | 10/2012 | Schoendorf ............ A61N 1/323 607/148 |
| 2016/0346546 A1* | 12/2016 | Zhu .................... A61N 1/36071 |
| 2017/0182324 A1* | 6/2017 | Carroll ................. A61N 1/3616 |
| 2017/0259069 A1 | 9/2017 | Baru et al. |
| 2018/0064943 A1 | 3/2018 | Grill et al. |
| 2019/0054306 A1* | 2/2019 | Steinke ................ A61N 1/3605 |
| 2019/0111267 A1* | 4/2019 | Chatalic ................ A61N 1/025 |

* cited by examiner

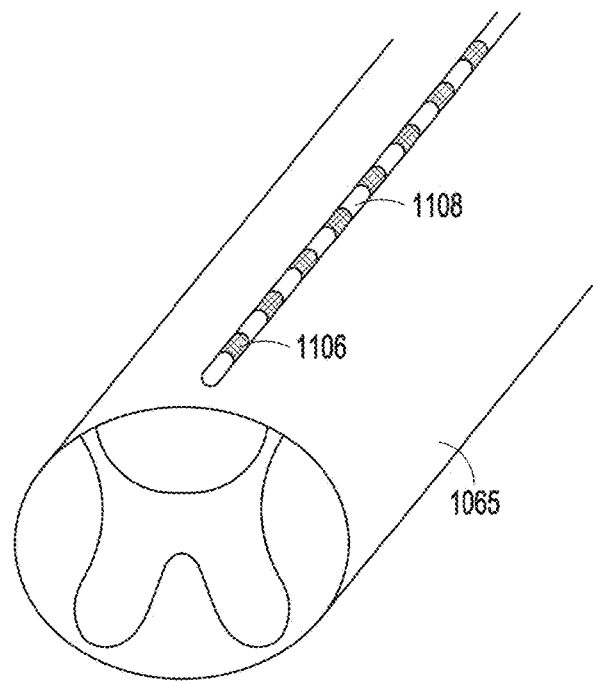
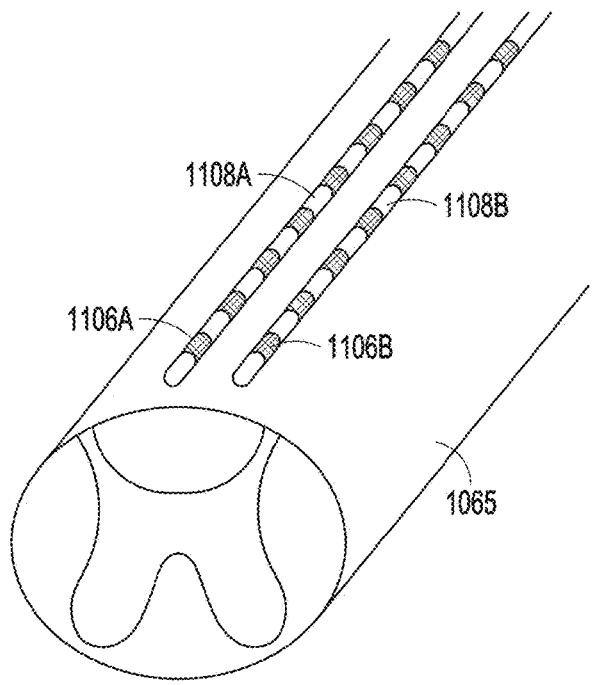
FIG. 10    FIG. 11
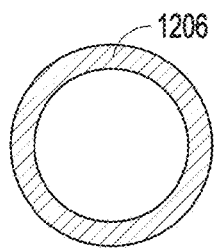 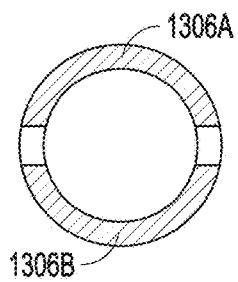 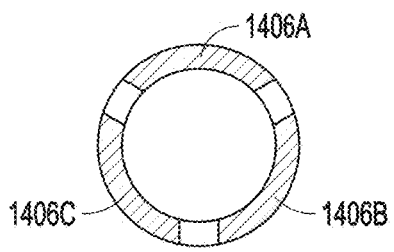
FIG. 12    FIG. 13    FIG. 14

INTERFERENTIAL STIMULATION METHOD AND SYSTEM FOR NEUROMODULATION

CLAIM OF PRIORITY

This application claims the benefit of priority under 35 U.S.C. § 119(e) of U.S. Provisional Patent Application Ser. No. 62/831,999, filed on Apr. 10, 2019, which is herein incorporated by reference in its entirety.

TECHNICAL FIELD

This document relates generally to medical devices and more particularly to a neuromodulation method and system providing for asynchronous and/or non-regular activation of neural fibers using interferential stimulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical signals. The delivery is controlled using stimulation parameters that specify spatial (where to stimulate), temporal (when to stimulate), and informational (patterns of stimulation directing the nervous system to respond as desired) aspects of a pattern of the electrical signals. Efficacy and efficiency of certain neurostimulation therapies can be improved, and their side-effects can be reduced, by determining these stimulation parameters based on a patient's conditions and therapeutic objectives. While modern electronics can accommodate the need for generating sophisticated signal patterns, the capability of a neurostimulation system depends on how stimulation parameters defining such a signal pattern can be determined and adjusted for the patient to ensure efficacy and efficiency of a therapy using neurostimulation when applied to the patient.

SUMMARY

An example (e.g., "Example 1") of a system for delivering neurostimulation energy to target tissue including nerve fibers using a plurality of electrodes may include a programming control circuit and a user interface. The programming control circuit may be configured to generate stimulation parameters controlling the delivery of the neurostimulation energy according to a neurostimulation program including a pattern of interferential stimulation configured to effect at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration. The user interface may be configured to determine the neurostimulation program and to provide the pattern of interferential stimulation with modulation of at least one of the first waveform, the second waveform, the first electrode configuration, or the second electrode configuration to result in a time-varying beat frequency capable of effecting the at least one of asynchronous activation of the nerve fibers or non-regular activation of the nerve fibers. The beat frequency is a difference between the first and second frequencies.

In Example 2, the subject matter of Example 1 may optionally be configured such that the user interface includes a presentation device configured to present user-programmable parameters, a user input device configured to allow for editing of the pattern of interferential stimulation by adjusting the user-programmable parameters, and a stimulation control circuit configured to determine the neurostimulation program including parameters defining the pattern of interferential stimulation using the user-programmable parameters.

In Example 3, the subject matter of Example 2 may optionally be configured such that the presentation device is further configured to present one or more effects of the user-programmable parameters in the pattern of interferential stimulation.

In Example 4, the subject matter of any one or any combination of Examples 2 and 3 may optionally be configured such that the stimulation control circuit is further configured to present a value for each parameter of the user-programmable parameters using the presentation device and to allow the user to change the displayed value using the user input device.

In Example 5, the subject matter of any one or any combination of Examples 2 to 4 may optionally be configured such that the stimulation control circuit is further configured to determine waveform parameters of the parameters defining the pattern of interferential stimulation, the waveform parameters defining the first waveform and the second waveform.

In Example 6, the subject matter of Example 5 may optionally be configured such that the stimulation control circuit is further configured to determine the waveform parameters including a first carrier frequency and a second carrier frequency for producing the first waveform using a first carrier waveform having the first carrier frequency and the second waveform using a second carrier waveform having the second carrier frequency.

In Example 7, the subject matter of Example 6 may optionally be configured such that the stimulation control circuit is further configured to determine the waveform parameters for at least one of producing the first waveform by modulating the first carrier waveform or producing the second waveform by modulating the second carrier waveform.

In Example 8, the subject matter of Example 7 may optionally be configured such that the stimulation control circuit is further configured to determine the waveform parameters for modulating at least one of the first carrier frequency or the second carrier frequency so that the at least one of the first career frequency or the second carrier frequency is time-varying.

In Example 9, the subject matter of Example 8 may optionally be configured such that the stimulation control circuit is further configured to determine a modulation range of the waveform parameters to be applied to the at least one of the first carrier frequency or the second carrier frequency. The modulation range is a range over which the at least one of the first carrier waveform or the second carrier waveform is modulated.

In Example 10, the subject matter of Example 9 may optionally be configured such that the stimulation control circuit is further configured to determine a modulation rate of the waveform parameters to be applied to the at least one of the first carrier frequency or the second carrier frequency. The modulation rate is a rate of change in time over which the at least one of the first carrier waveform or the second carrier waveform is modulated.

In Example 11, the subject matter of Example 10 may optionally be configured such that the stimulation control circuit is further configured to determine a modulation type specifying a manner in which the at least one of the first carrier waveform or the second carrier waveform is modulated.

In Example 12, the subject matter of any one or any combination of Examples 2 to 11 may optionally be configured such that the stimulation control circuit is further configured to determine field parameters of the parameters defining the pattern of interferential stimulation, the field parameters defining the first electrode configuration and the second electrode configuration.

In Example 13, the subject matter of Example 12 may optionally be configured such that the stimulation control circuit is further configured to determine the field parameters for making at least one of the first electrode configuration or the second electrode configuration time-varying.

In Example 14, the subject matter of Example 13 may optionally be configured such that the stimulation control circuit is configured to determine the field parameters for modulating a percentage of stimulation current flowing through each electrode of the plurality of electrodes for the at least one of the first electrode configuration or the second electrode configuration such that the percentage is time-varying.

In Example 15, the subject matter of Example 13 may optionally be configured such that the stimulation control circuit is further configured to determine the field parameters to provide for an asymmetric stimulation field for focusing the delivery of the neurostimulation energy to a region of the target tissue, the region varying with the time-varying at least one of the first electrode configuration or the second electrode configuration.

An example (e.g., "Example 16") of a method for delivering neurostimulation energy to target tissue including nerve fibers using a plurality of electrodes is also provided. The method may include determining a pattern of interferential stimulation for effecting at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration and by modulating at least one of the first waveform, the second waveform, the first electrode configuration, or the second electrode configuration to result in a time-varying beat frequency capable of effecting the at least one of asynchronous activation of the nerve fibers or non-regular activation of the nerve fibers. The beat frequency is a difference between the first and second frequencies. The method may further include determining a neurostimulation program based on the determined pattern of interferential stimulation and generating stimulation parameters for controlling the delivery of the neurostimulation energy according to the determined neurostimulation program.

In Example 17, the subject matter of Example 16 may optionally further include transmitting the generated stimulation parameters to an implantable stimulation device, delivering the neurostimulation energy from the implantable stimulation device, and controlling the delivery of the neurostimulation energy using the stimulation parameters received by the implantable stimulation device.

In Example 18, the subject matter of any one or any combination of Examples 16 and 17 may optionally include presenting user-programmable parameters using a presentation device, presenting one or more effects of the user-programmable parameters in the pattern of interferential stimulation using the presentation device, allowing a user to edit the pattern of interferential stimulation by adjusting the user-programmable parameters based on the presented one or more effects, and determining parameters defining the pattern of interferential stimulation using the user-programmable parameters.

In Example 19, the subject matter of determining the parameters defining the pattern of interferential stimulation as found in Example 18 may optionally include determining waveform parameters defining the first waveform and the second waveform. The waveform parameters include a first carrier frequency and a second carrier frequency for producing the first waveform using a first carrier waveform having the first carrier frequency and the second waveform using a second carrier waveform having the second carrier frequency.

In Example 20, the subject matter of determining the waveform parameters as found in Example 19 may optionally further include determining the waveform parameters for at least one of producing the first waveform by modulating the first carrier waveform or producing the second waveform by modulating the second carrier waveform.

In Example 21, the subject matter of determining the waveform parameters as found in Example 20 may optionally further include determining the waveform parameters for modulating at least one of the first carrier frequency or the second carrier frequency so that the at least one of the first career frequency or the second carrier frequency is time-varying.

In Example 22, the subject matter of determining the waveform parameters as found in Example 21 may optionally further include at least one of determining a modulation range of the waveform parameters to be applied to the at least one of the first carrier frequency or the second carrier frequency, determining a modulation rate of the waveform parameters to be applied to the at least one of the first carrier frequency or the second carrier frequency, and a modulation type specifying a manner in which the at least one of the first carrier waveform or the second carrier waveform is modulated. The modulation range is a range over which the at least one of the first carrier waveform or the second carrier waveform is modulated. The modulation rate is a rate of change in time over which the at least one of the first carrier waveform or the second carrier waveform is modulated.

In Example 23, the subject matter of determining the parameters defining the pattern of interferential stimulation as found in any one or any combination of Examples 18 to 22 may optionally include determining field parameters of the parameters defining the pattern of interferential stimulation. The field parameters define the first electrode configuration and the second electrode configuration.

In Example 24, the subject matter of determining the field parameters as found in Example 23 may optionally include determining the field parameters for making at least one of the first electrode configuration or the second electrode configuration time-varying.

An example (e.g., "Example 25") of a non-transitory computer-readable storage medium including instructions, which when executed by a system, cause the system to perform a method for delivering neurostimulation energy is also provided. The method may include determining a pattern of interferential stimulation for effecting at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration and by modulating at least one of the first waveform, the second waveform, the first electrode configuration, or the second electrode configuration to result in a time-varying beat frequency capable of effecting the at least one of asynchronous activation of the nerve fibers or non-regular activation of the nerve fibers. The beat frequency is a difference between the first and second frequencies. The method may further include determining a neurostimulation program based on the determined pattern of interferential stimulation and generating stimulation parameters for controlling the delivery of the neurostimulation energy according to the determined neurostimulation program.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 10 illustrates an embodiment of electrodes on a lead placed for use with a stimulation device, such as the stimulation device of FIG. 9.

FIG. 11 illustrates an embodiment of electrodes on two leads placed for use with a stimulation device, such as the stimulation device of FIG. 9.

FIG. 12 illustrates an embodiment of electrodes in a cross-sectional view of a lead, such as one of the leads shown in FIG. 10 or FIG. 11.

FIG. 13 illustrates another embodiment of electrodes in a cross-sectional view of a lead, such as one of the leads shown in FIG. 10 or FIG. 11.

FIG. 14 illustrates another embodiment of electrodes in a cross-sectional view of a lead, such as one of the leads shown in FIG. 10 or FIG. 11.

DETAILED DESCRIPTION

Figure 1:
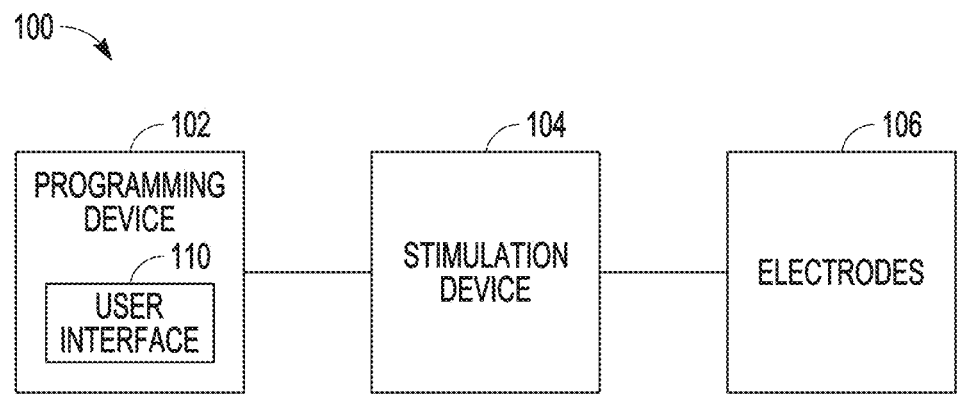
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can deliver interferential stimulation for asynchronous and/or non-regular activation of neural fibers in a patient. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device.

Asynchronous activation includes activation of neural fibers in an asynchronous manner in response to a stimulus. In asynchronous activation, two or more axons exhibit different firing patterns in response to the same stimulus. Non-regular activation includes activation of neural fibers in a non-regular manner in response to a stimulus. In non-regular activation, a single axon fires at a varying rate (or inter-spike interval). For example, in response to an electrical pulse in SCS delivered to a patient, the fibers in the patient's dorsal column can be selectively activated and with various delays, depending on the pulse waveform and the site of delivery. Such phenomena can be used to select stimulation parameters for sub-perception neurostimulation for pain control by sufficiently activating the patient's dorsal horn fibers to effect pain suppression without activating the dorsal column fibers to an extent causing paresthesia. While SCS for pain management is discussed as a specific example, the present subject matter can also be applied to program stimulation devices for delivering various types of neuromodulation therapies.

Biphasic rectangular waveforms (pulses) applied at low frequencies over specific dorsal column sites have been found to produce clinical efficacy at sub-perception amplitudes with substantial energy savings. An example is discussed in U.S. patent application Ser. No. 16/100,904, filed on Aug. 10, 2018, assigned to Boston Scientific Neuromodulation Corporation, which is incorporated by reference herein in its entirety. Paresthesia-based placement suggests that staggered dorsal column activation is involved, with biphasic rectangular waveform with both stimulation and recharge phases of a biphasic waveform actively driven and delivered through the same electrodes. Other stimulation strategies, such as discussed in U.S. Patent Application Publication No. 2018/0064943 A1, can also be used to circumvent this method.

Interferential stimulation can activate neural tissue using two or more waves having sinusoidal frequencies offset by a "beat frequency" and applied through multiple electrode pairs to create time and directionally varying electric fields. For example, applying two sinusoidal waveforms having frequencies f1 and f2 to tissue through two pairs of electrodes results in activation functions (AFs) in X and Y directions ($AF_X$ and $AF_Y$) in space at an arbitrary point (see examples illustrated in FIGS. 16-23). The beat frequency ($f_b$) is equal to the absolute value of the difference of the two carrier frequencies (i.e., $f_b=|f2-f1|$). This beat frequency determines neural activation by producing "pulses" and stands in for an effective temporal pattern of pulses. Electrode geometries and different phasing of waveforms can result in different focal points where effects of the interferential stimulation are maximized. The magnitude and direction of electric field at a given time in space and the location where the gradient of the electric field is the largest vary with the envelope waveforms and the beat frequency.

Beat frequencies created during interferential stimulation can result in asynchronous and/or non-regular activation of neural elements in such a manner as to produce effects similar to the examples discussed in U.S. patent application Ser. No. 16/100,904. The present subject matter provides systems and methods for modulating the fundamental components of the beat frequency in a time-varying manner to produce an "irregular" beat frequency that varies with time and produces asynchronous and/or non-regular activation of target neural fibers. The time-varying beat frequency can result from varying (e.g., modulating) either or both of the carrier frequencies. Interferential stimulation using two sinusoidal waveforms with frequencies $f1(t)$ and $f2(t)$ are specifically discussed as examples for illustration and discussion. However, the present subject matter is neither limited to two waveforms nor limited to sinusoidal waveforms. In various embodiments, the interferential stimulation according to the present subject matter can use two or more waveforms to produce activation functions with a beat frequency that varies with time.

In various embodiments, the frequencies $f1(t)$ and $f2(t)$ are functions varying with time. To produce waveforms with the frequencies $f1(t)$ and $f2(t)$, sinusoidal carrier waveforms with frequencies F1 and F2 can be modulated, respectively. The carrier waveforms can be modulated in several different ways, independently or concurrently (e.g., as selected by the user using the selection boxes), with several important parameters (e.g., modulation type, modulation range, and modulation rate). Activation functions (e.g., $AF_X$ and $AF_Y$) depend on peak, trough, and amplitude of the beat frequency (which is a function of the modulated carrier frequencies $f1(t)$ and $f2(t)$).

In this document, a "patient" includes a person receiving treatment delivered using a neurostimulation system according to the present subject matter, and a "user" includes a physician or other caregiver who treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
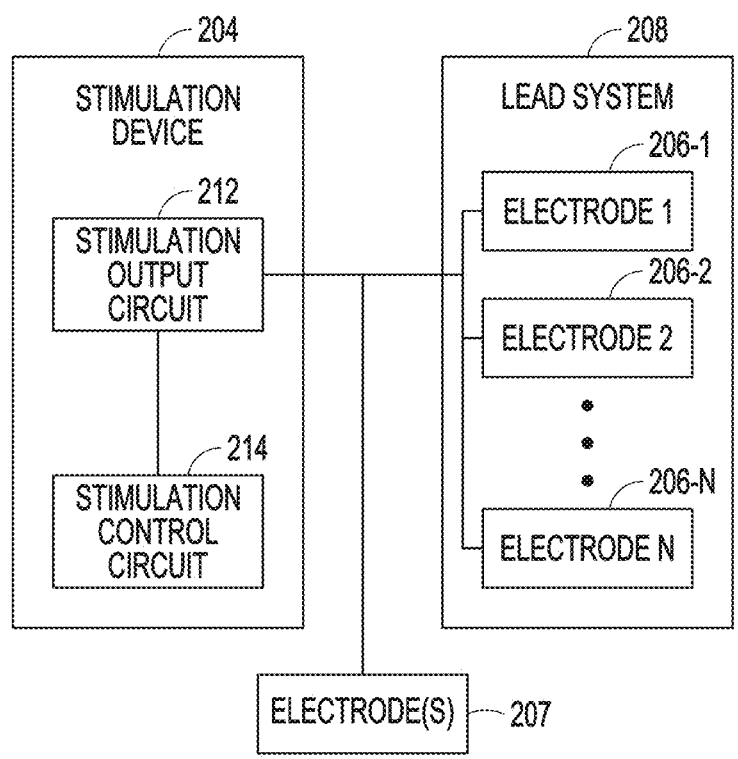
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
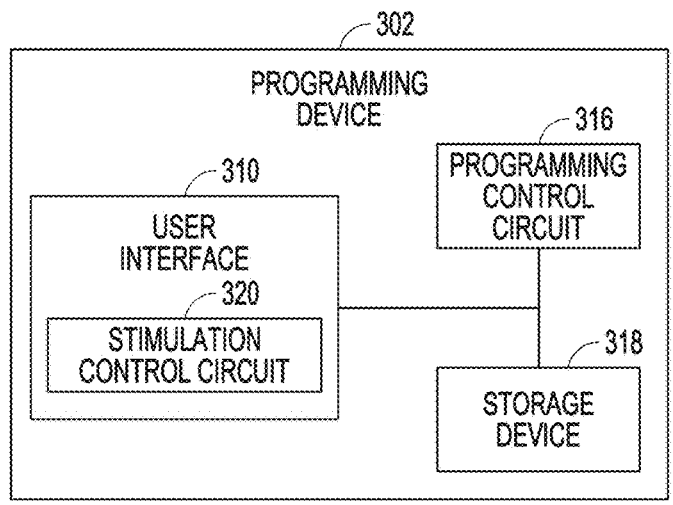
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
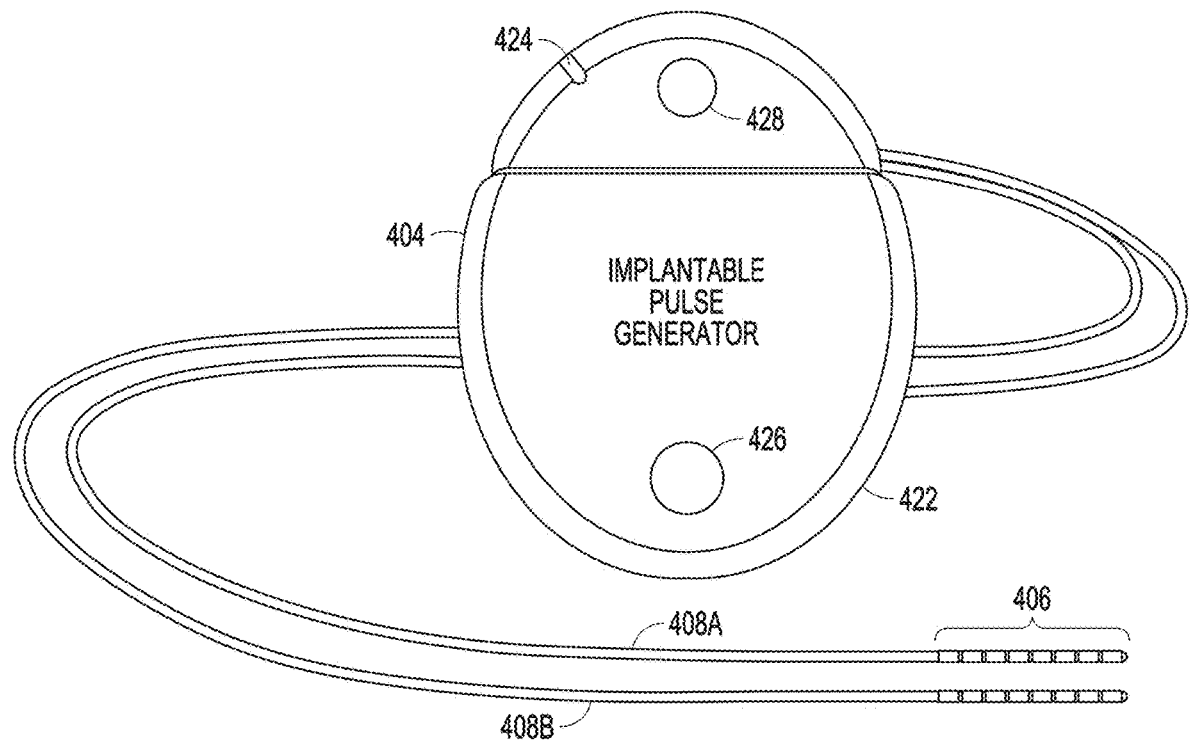
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to a nerve cell target included in the subject's spinal cord.

Figure 5:
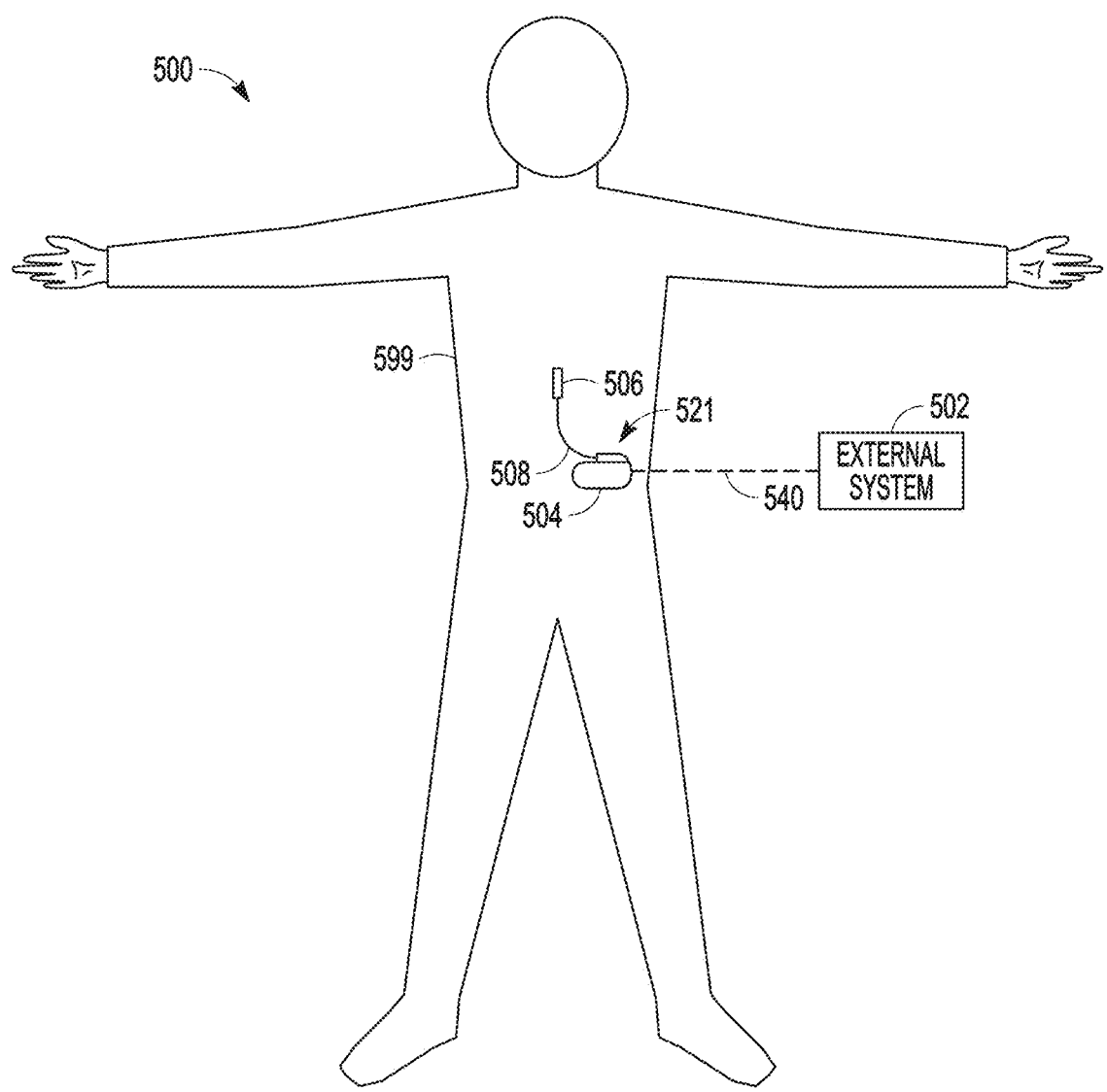
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
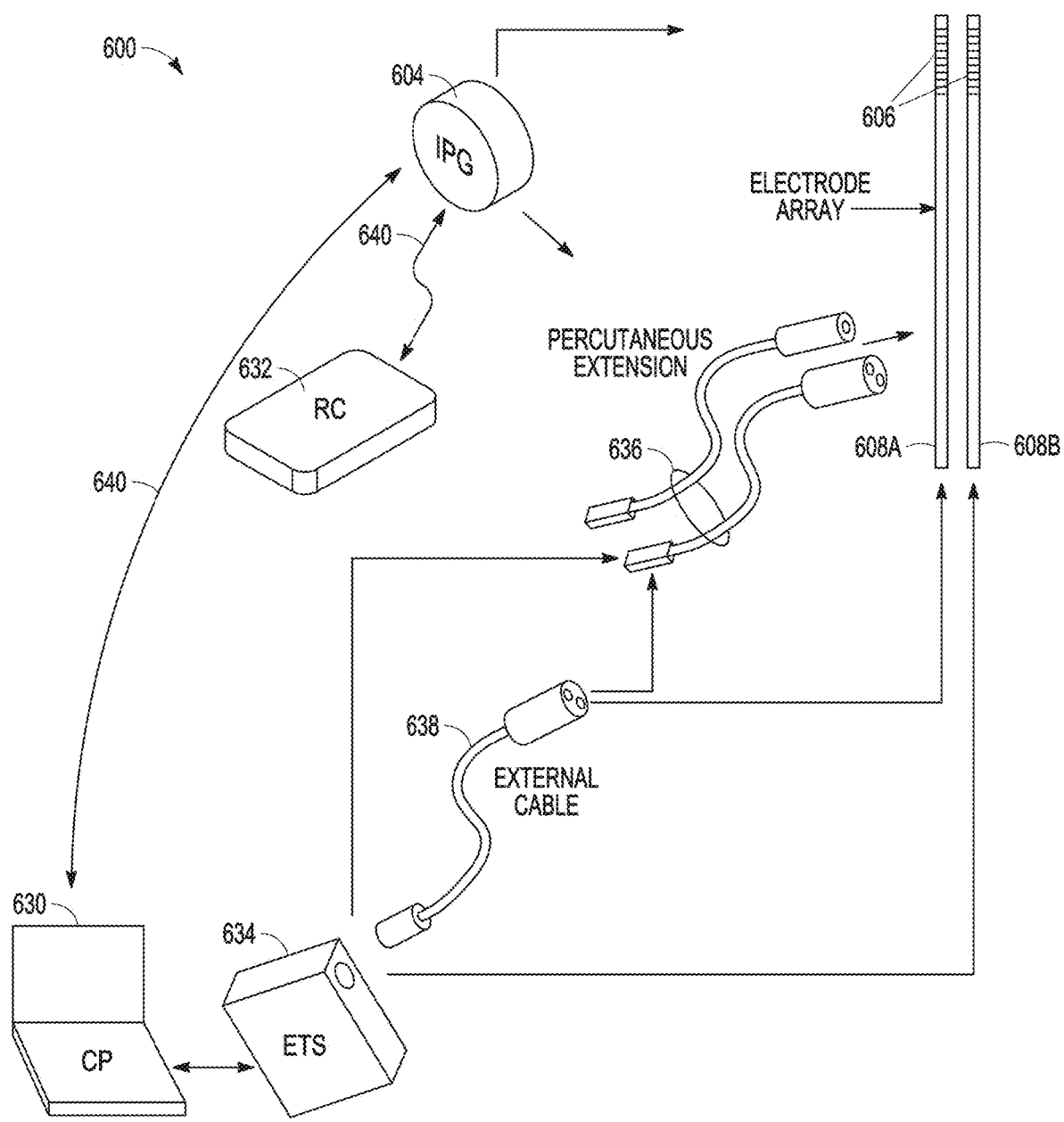
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634, If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340, RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
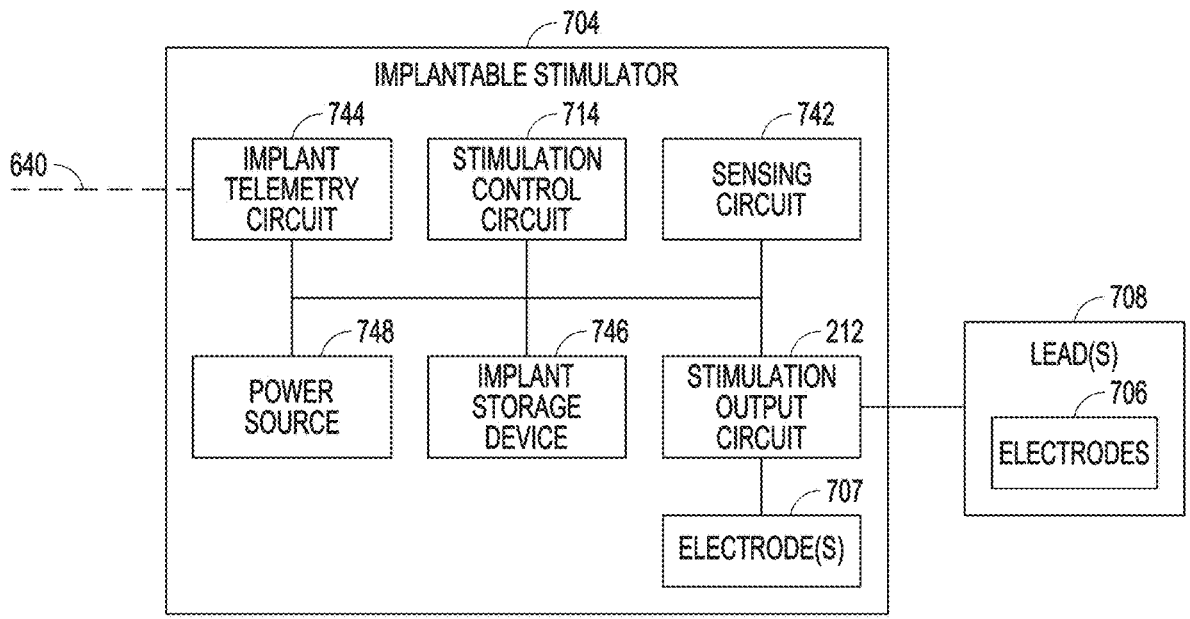
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
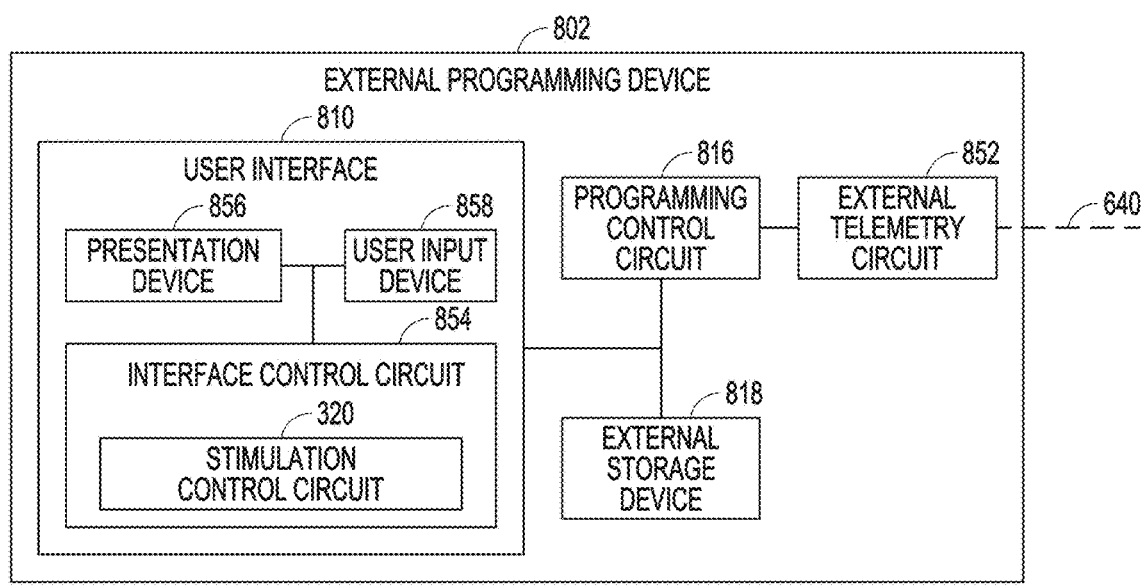
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
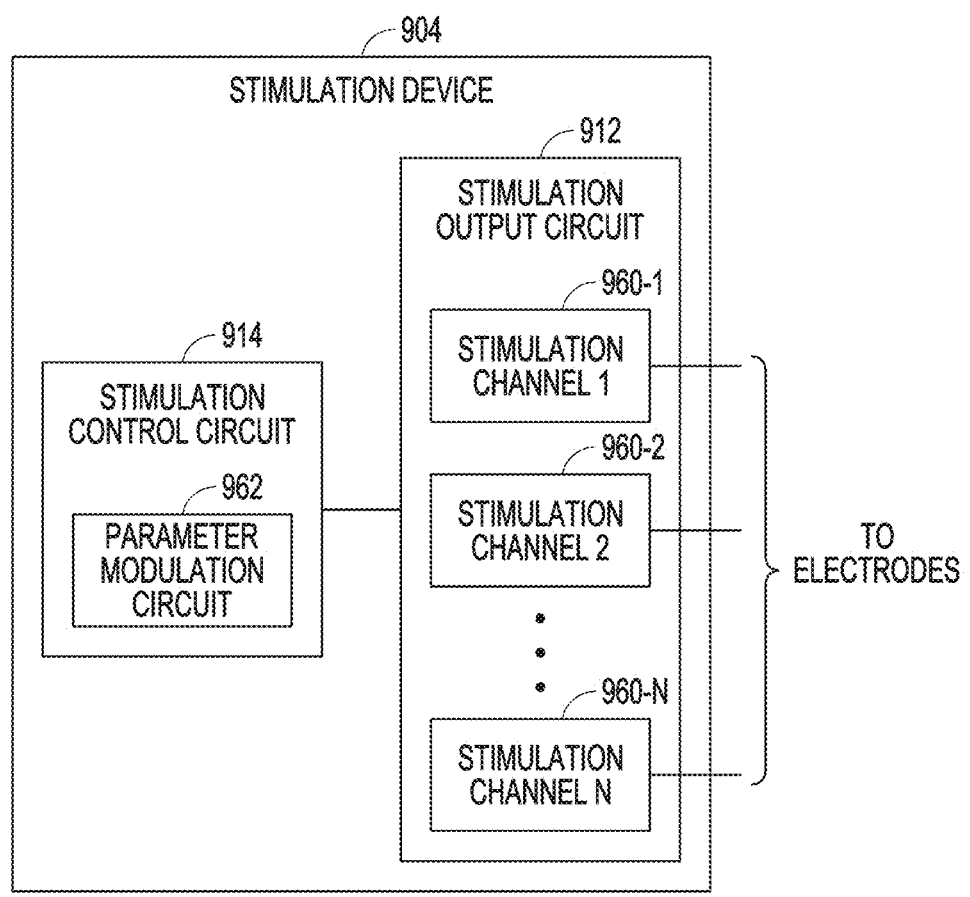
FIG. 9 illustrates an embodiment of a stimulation device for delivering interferential stimulation.

FIG. 9 illustrates an embodiment of a stimulation device 904 for delivering interferential stimulation. Stimulation device 904 can be included in any of the stimulation devices discussed in this document, including but not limited to stimulation devices (including implantable stimulators and IPGs) 104, 204, 404, 504, 604, and 704. In various embodiments, stimulation devices 904 can deliver neurostimulation energy to a neural target including nerve fibers using a plurality of electrodes, such as electrodes selected from those discussed in this document, including but not limited to electrodes 106, 206, 207, 406, 426, 428, 506, 606, 706, and 707.

Stimulation device 904 includes a stimulation output circuit 914 and a stimulation control circuit 914. Stimulation output circuit 912 can represent an example of stimulation output circuit 212. Stimulation control circuit 914 can represent an example of stimulation control circuit 214 or 714.

Stimulation output circuit 912 can include stimulation channels 960-1 to 960-N each producing a stimulation current and delivering that stimulation current using electrodes selected from the plurality of electrodes. In a 2-channel example, 2 of the stimulation channels 960-1 to 960-N are used for interferential stimulation. A first stimulation channel (e.g., stimulation channel 960-1) can be configured to produce a first stimulation current and to deliver the first stimulation current to the tissue using a first electrode configuration, and a second stimulation channel (e.g., stimulation channel 960-2) can be configured to produce a second stimulation current and to deliver the second stimulation current to the tissue using a second electrode configuration. The first stimulation current has a first waveform with a first frequency. The second stimulation current has a second waveform with a second frequency. The first electrode configuration can be specified for effecting a distribution of the first stimulation current in each electrode of the plurality of electrodes. The second electrode configuration can be specified for effecting a distribution of the second stimulation current in each electrode of the plurality of electrodes. While the 2-channel example is discussed below as a specific example for illustrative rather than restrictive purposes, the number N can be two or larger in various embodiments. In other words, n channels ($2 \leq n \leq N$) can be selected for interferential stimulation. Each selected stimulation channel i ($1 \leq i \leq N$) is configured to produce an $i^{th}$ stimulation current having an $i^{th}$ waveform with an $i^{th}$ frequency and to deliver the $i^{th}$ stimulation current to the tissue using an $i^{th}$ electrode configuration specified for effecting a distribution of the $i^{th}$ stimulation current in each electrode of the plurality of electrodes. In this document, "electrode configuration" can also be referred to as "electrode geometry" and can be defined by, for example, specifying selective activation of electrodes or fractionalization.

Stimulation control circuit 914 includes a parameter modulation circuit 962. In the 2-channel example, stimulation control circuit 914 can control the generation and delivery of the first and second stimulation currents using stimulation parameters according a neurostimulation program including a pattern of interferential stimulation. Parameter modulation circuit 962 can modulate at least one of the first waveform, the second waveform, the first electrode configuration, or the second electrode configuration to result in the pattern of interferential stimulation including a time-varying beat frequency capable of effecting asynchronous and/or non-regular activation of the nerve fibers when the first and second stimulation currents are delivered simultaneously. The beat frequency being a difference between the first and second frequencies.

In one embodiment, stimulation output circuit 912 produces the first waveform using a first carrier waveform having a first carrier frequency and to produce the second waveform using a second carrier waveform having a second carrier frequency. Parameter modulation circuit 962 modulates at least one of the first waveform or the second waveform so that at least one parameter of the at least one of the first waveform or the second waveform is time-varying. In one embodiment, parameter modulation circuit 962 modulates at least one of the first carrier waveform or the second carrier waveform. In one embodiment, parameter modulation circuit 962 modulates at least one of the first carrier frequency or the second carrier frequency so that the at least one of the first career frequency or the second carrier frequency is time-varying. This can be done by, for example, applying a modulation range to the at least one of the first carrier frequency or the second carrier frequency, applying a modulation rate to the at least one of the first carrier frequency or the second carrier frequency, and/or modulating at least one of the first carrier waveform or the second carrier waveform according to a specified type of modulation. The modulation range is a range over which the at least one of the first carrier waveform or the second carrier waveform is modulated. The modulation rate is a rate of change in time over which the at least one of the first carrier waveform or the second carrier waveform is modulated. The waveform parameters including the first and second carrier frequencies, the modulation range, the modulation rate, and the modulation type are further discussed below, with references to FIG. 16. In one embodiment, parameter modulation circuit 962 modulates at least one of the first electrode configuration or the second electrode configuration so that the at least one of the first electrode configuration or the second electrode configuration is time-varying. This can be done by, for example, modulating a selection of active electrodes from the plurality of electrodes or modulating a percentage of stimulation current flowing through each electrode of the plurality of electrodes.

FIG. 10 illustrates an embodiment of electrodes 1006 on a lead 1008 placed on or adjacent to a spinal cord 1065 for use with a stimulation device such as stimulation device 904. FIG. 11 illustrates another embodiment of electrodes 1106A on a lead 1108A and 1106B on a lead 1108B placed on or adjacent to the spinal cord 1065 for use with the stimulation device. As illustrated in FIGS. 10 and 11, each of leads 1008, 1108A, and 1108B has an elongated body with an array of electrodes 1006, 1108A, and 1108B, respectively, incorporated onto its distal end. FIGS. 12-14 each illustrate an embodiment of electrodes 1006, 1108A, or 1108B shown in a cross-sectional view of a lead in a plane perpendicular to the longitudinal axis of the lead (i.e., transverse view). Conductive wires extending within the elongated body provide for electrical connections between the electrodes and the stimulation device when the lead is connected to the stimulation device. FIG. 12 illustrates an embodiment of a ring electrode 1206. In some embodiments, leads 1008, 1108A, and/or 1108B can each be a directional lead that includes at least some segmented electrodes circumferentially disposed about the directional lead. FIG. 13 illustrates an embodiment of 2-segmented electrodes 1306A and 1306B distributed along a circumference of the lead. FIG. 14 illustrates an embodiment of 3-segmented electrodes 1406A, 1406B, and 1406C distributed along a circumference of the lead. In various embodiments, the number and shape of leads and electrodes can vary according to the intended application.

Electrodes 1006 on lead 1008, electrodes 1106A on lead 1108A, and electrodes 1106B on lead 1108B, and electrodes 1206, 1306A-B, and 1406A-C are shown in FIGS. 10-14 as specific examples for illustrative rather than restrictive purposes. While FIGS. 10 and 11 illustrate leads with placements for SCS, the present application matter can be applied to stimulation of any neural tissue with leads and electrodes placed according to the intended target. In various embodiments, the plurality of electrodes selectable for delivering interferential stimulation according to the present subject matter can include any suitable forms of electrodes on leads and/or the stimulation device, and the leads can include, but are not limited to, percutaneous and/or implantable leads with electrodes incorporated into a distal portion that is suitable for epidural and/or intradural placement. In various embodiments, each electrode configuration as discussed in this document can be specified for effecting a distribution of the stimulation current in each electrode of the plurality of electrodes.

The electrode configuration can be specified to result in a symmetric stimulation field (e.g., using lead 1008 with one or more of electrodes 1006 in the form of electrode 1206) or an asymmetric stimulation field (e.g., using leads 1108A and 1108B with one or more of electrodes 1106A and one or more electrodes 1106B in the form of electrodes 1306A-B and/or electrodes 1406A-C). In some embodiments, use of directional leads to deliver interferential stimulation with certain electrode configuration can allow for lateral and focal selectivity (e.g., an asymmetric stimulation field that selectively activates neural elements, such as fibers, cells, terminals, and other elements in the spinal cord, on one side or one point).

Figure 15:
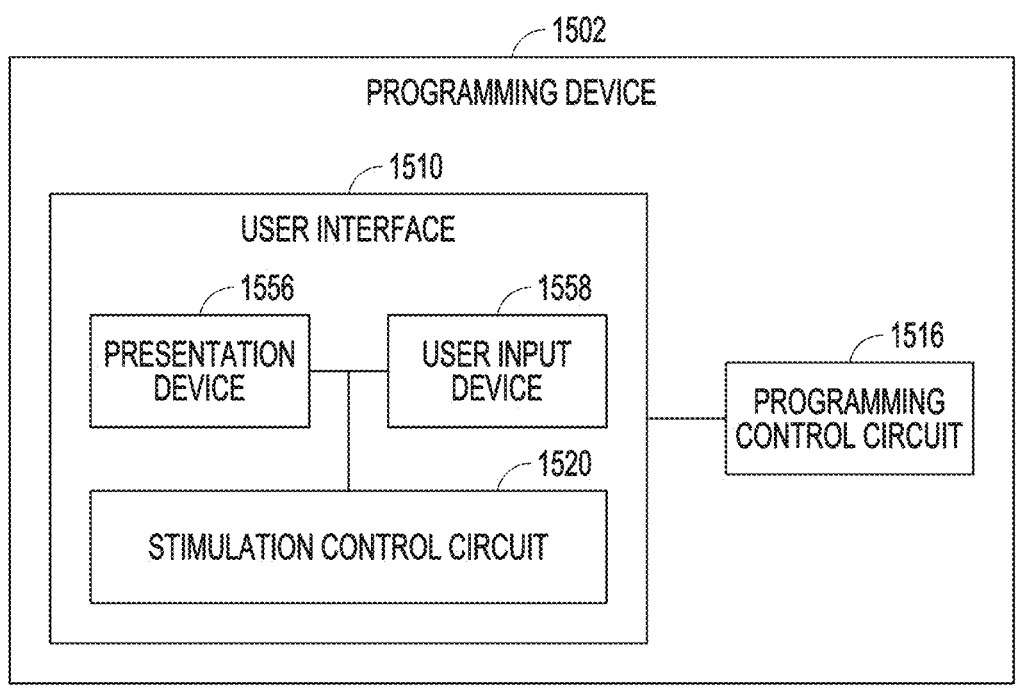
FIG. 15 illustrates an embodiment of a programming device for programming a stimulation device, such as the stimulation device of FIG. 9.

FIG. 15 illustrates an embodiment of a programming device 1502 for programming a stimulation device, such as stimulation device 904. Programming device 1502 can be included in any of the programming devices discussed in this document, including but not limited to programming devices (including external system) 102, 302, 502, 630, 632, and 802.

Programming device 1502 can include a programming control circuit 1516 and a user interface 1510. Programming control circuit 1516 can represent an example of programming control circuit 316 or 816. User interface can represent an example of user interface 110, 310, or 810.

Programming control circuit 1516 can generate the stimulation parameters according to the neurostimulation program including the pattern of interferential stimulation configured to effect asynchronous and/or non-regular activation of the nerve fibers, such as the stimulation parameters used by stimulation device 904. As discussed above for stimulation device 904, the interferential stimulation can result from simultaneously delivering the first stimulation current to the tissue using the first electrode configuration and the second stimulation current to the tissue using a second electrode configuration.

User interface 1510 can determine the neurostimulation program. It can allow the user to compose the neurostimulation program. The neurostimulation program can provide the pattern of interferential stimulation with modulation of at least one of the first waveform, the second waveform, the first electrode configuration, or the second electrode configuration to result in a time-varying beat frequency capable of effecting asynchronous and/or non-regular activation of the nerve fibers.

User interface 1510 can include a presentation device 1556, a user input device 1558, and a stimulation control circuit 1520. Presentation device 1556 can represent an example of presentation device 856 and can present user-programmable parameters and one or more effects of the user-programmable parameters in the pattern of interferential stimulation. User input device 1558 can represent user input device 858 and can allow the user to create and edit the pattern of interferential stimulation by setting and adjusting the user-programmable parameters. Stimulation control circuit 1520 can represent an example of stimulation control circuit 320 and can determine the neurostimulation program including parameters defining the pattern of interferential stimulation using the user-programmable parameters.

In various embodiments, stimulation control circuit 1520 can display a value for each parameter of the user-programmable parameters using presentation device 1556 and to allow the user to change the displayed value using user input device 1558. The pattern of interferential stimulation can be defined using parameters including waveform parameters and field parameters. The waveform parameters and field parameters can each be a user-programmable parameter or be derived from one or more user-programmable parameters. The waveform parameters define the stimulation waveforms (e.g., the first waveform and the second waveform in the 2-channel example). The stimulation waveforms each define a temporal pattern of the neuromodulation energy to be delivered. The field parameters define the electrode configurations (e.g., the first electrode configuration and the second electrode configuration in the 2-channel example). The electrode configurations (or electrode geometry, corresponding to the stimulation fields as discussed above) each defining a spatial distribution of the neurostimulation energy across the plurality of electrodes. In various embodiments, stimulation control circuit 1520 can determine the waveform parameters for modulating at least one waveform parameter so that the waveform parameter is time-varying. For example, stimulation control circuit 1520 can determine the waveform parameter for modulating the frequency of a waveform so that the frequency is time-varying. Stimulation control circuit 1520 can also determine the field parameters for modulating a field parameter so that an electrode configuration is time-varying. This can be done by, for example, modulating a selection of active electrodes for the electrode configuration or modulating a percentage of stimulation current flowing through each electrode of the plurality of electrodes for the electrode configuration.

Figure 16:
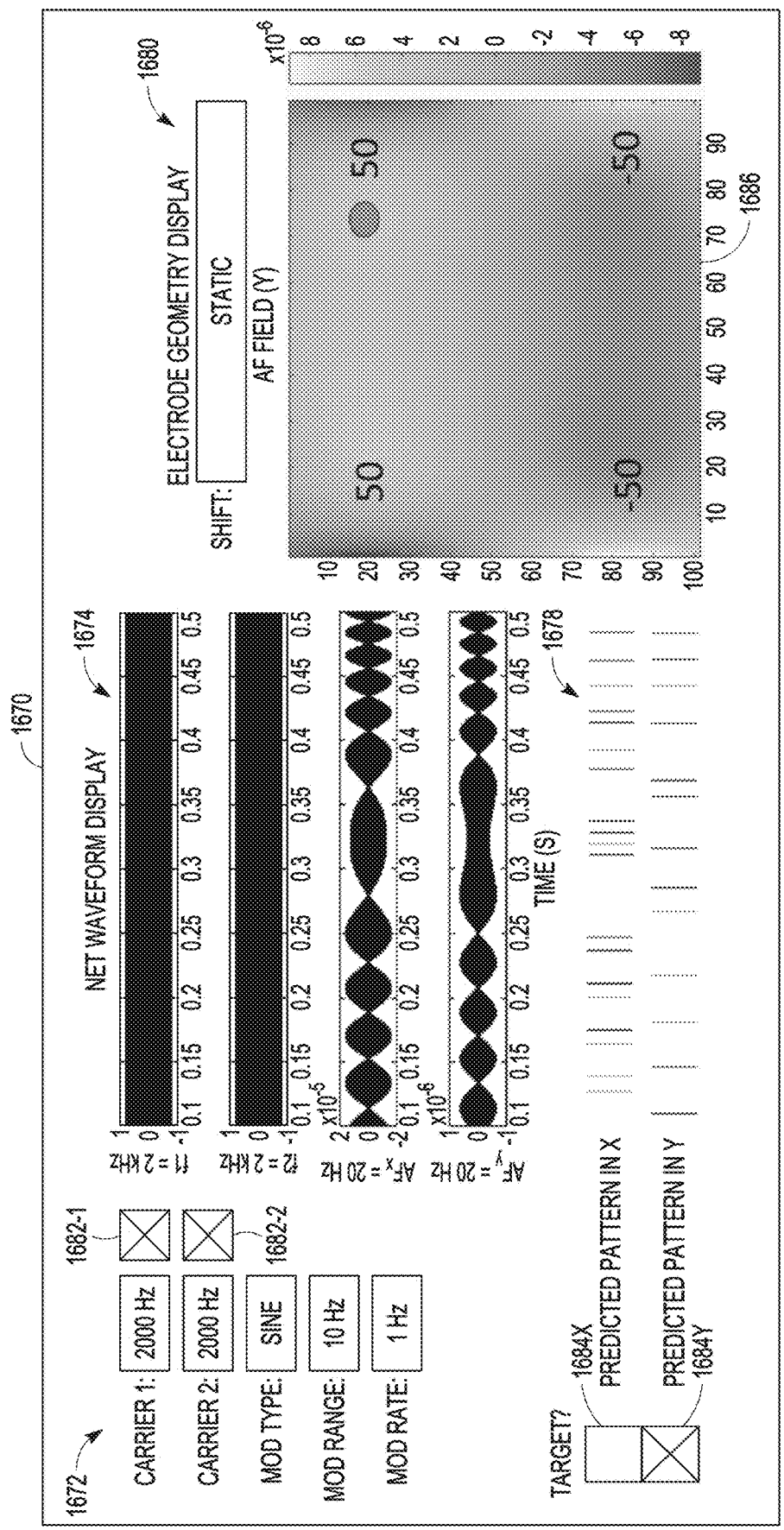
FIG. 16 illustrates an embodiment of a display screen allowing for programming the stimulation device for interferential stimulation, such as part of the programming device of FIG. 15.

FIG. 16 illustrates an embodiment of a display screen 1670 allowing for programming the stimulation device for interferential stimulation. Screen 1670 can be part of presentation device 1556. Screen 1670 as illustrated in FIG. 16 can represent portions of a display screen of presentation device 1556, such as a window or other display area configured for programming the stimulation device, such as stimulation device 904, the interferential stimulation. Design including layout of screen 1670 as shown in FIGS. 16-23 represents an example for illustrative rather than restrictive purposes. Contents of screen 1670 (e.g., examples of user-adjustable parameters) as shown in FIGS. 16-23 also represent an example for illustrative rather than restrictive purposes.

In the illustrated embodiment, screen 1670 includes a parameters area 1672, a net waveform display area 1674, a net pattern display area 1678, and an electrode geometry display area 1680. The user-adjustable parameters displayed in parameters area 1672 to allow for adjustments by the user include:

Carrier 1 (F1): carrier frequency (i.e., unmodulated) of the sinusoidal carrier wave that exits a first electrode;
  Carrier 2 (F2): carrier frequency (i.e., unmodulated) of the sinusoidal carrier wave that exits a second electrode (e.g., difference between carrier frequencies F1 and F2 should be less than 200 Hz to avoid refractoriness);
  Modulation range ("Mod Range"): Range (R, Hz) over which modulation of the carrier waveform(s) happens (e.g., modulation range should be less than 100 Hz to avoid refractoriness, which is defined as 200 Hz, a typical upper limit of continuous firing of dorsal column fibers, to allow the interferential stimulation waveforms to be time-varying within predefined boundaries);
  Modulation rate ("Mod Rate"): Rate of change ($\Delta$, Hz) in time over which modulation of the carrier waveform(s) happens (e.g., modulation rate may be variable but should be less than 0.25 times the modulation range to avoid pattern shifting too quickly); and
  Modulation type ("Mod Type"): Manner in which either and/or both of the carrier waveforms are modulated over time.

Examples of the modulation type include:
  Sinusoidal modulation type: $f(t)=\sin(2\cdot\pi\cdot(F+R\cdot\sin(2\cdot\pi\cdot\Delta\cdot t))\cdot t)$;
  Sawtooth modulation type: $f(t)=\sin(2\cdot\pi\cdot(\text{linear variation in } F)\cdot t)$;
  Noisy modulation type: $f(t)=\sin(2\cdot\pi\cdot(F+R\cdot\text{Ornstein-Uhlenbeck}(\Delta, t))\cdot t)$,
  Fixed (or variable) Phase Delays $f(t)=\sin(2\cdot\pi\cdot F\cdot(t-1000/\Delta(t)))$; and
  Other variation functions, wrapping carriers and beat function around another e.g., amplitude or step function envelope, also possible.

In these examples:
  f(t) can be f1(*t*) or f2(*t*) with F1 being the corresponding carrier frequency F1 or F2;
  R is modulation range in Hz;
  $\Delta$ is modulation rate in Hz;
  t is time; and
  The Ornstein-Uhlenbeck noise has a continuous derivative whose rate of random change is defined by "relaxation" and "diffusion" times, which can both be tied to A through a look up table.

User-selection boxes 1682 allow either or both of the carrier sinusoidal waveforms (with carrier frequencies F1 and F2) to be selected for modulation. If box 1682-1 is selected, the carrier sinusoidal waveform with carrier frequency F1 will be modulated. If box 1682-2 is selected, the carrier sinusoidal waveform with carrier frequency F2 will be modulated.

Net waveform display area 1674 displays the two sinusoidal carrier waveforms and the modulated waveforms showing the beat frequencies in X and Y directions. Net pattern display area 1678 displays predicted patterns in the X and Y directions. The X and Y directions correspond to X and Y axes in a geometrical coordinate system allowing for analysis of electrode geometry and associated stimulation field distribution or volume of tissue activation. For example, the X and Y directions can correspond to the longitudinal and transverse directions of a lead. Target selection boxes 1684 allow the user to select target for display in electrode geometry display area 1680, which displays a predicted activation function (AF) field 1686 at time point for a desired target and geometry, with color, gray scale, or other indicators representing field strength. When box 1684X is selected, AF field 1686 as displayed in the AF field in X direction ($AF_X$). When box 1684Y is selected, AF field 1686 as displayed in the AF field in Y direction ($AF_Y$). The predicted pattern in X and Y directions show symbols representing action potentials indicating activation pattern in an axon in X and Y directions, respectively.

Electrode geometry display area 1670 also allows the user to specify whether the electrode configuration is to be modulated. In the illustrated example, the user can select a type of "shift" in the electrode geometry. Examples of types of such shift include:
  Static: the electrode geometry does not change over time (e.g., in FIG. 16);
  Counter-clock: the electrode geometry rotates counter-clockwise over time (e.g., in FIGS. 20-22);
  Clock: the electrode geometry rotates clockwise over time; and
  Any weave patterns with the focal point configured to "bounce" left and right and/or rostrally or caudally along the electrode.

In various embodiments, the purpose of shifting the electrode geometry is to move the focal point in such a way as to cause different populations of neural fibers to activate at different times and/or to cause a particular group of neural fibers to fire on a specific pattern. The effects of various electrode configurations can be observed in the displayed AF field 1686, which will show, for example, the stimulation field being symmetric or asymmetric (e.g., lateral or focal) as intended with each electrode configuration. The predicted and displayed AF field 1686 is a function of spatial location. Thus, changing a spatial location to be observed ("probed") can change the pattern that is displayed.

Figure 17:
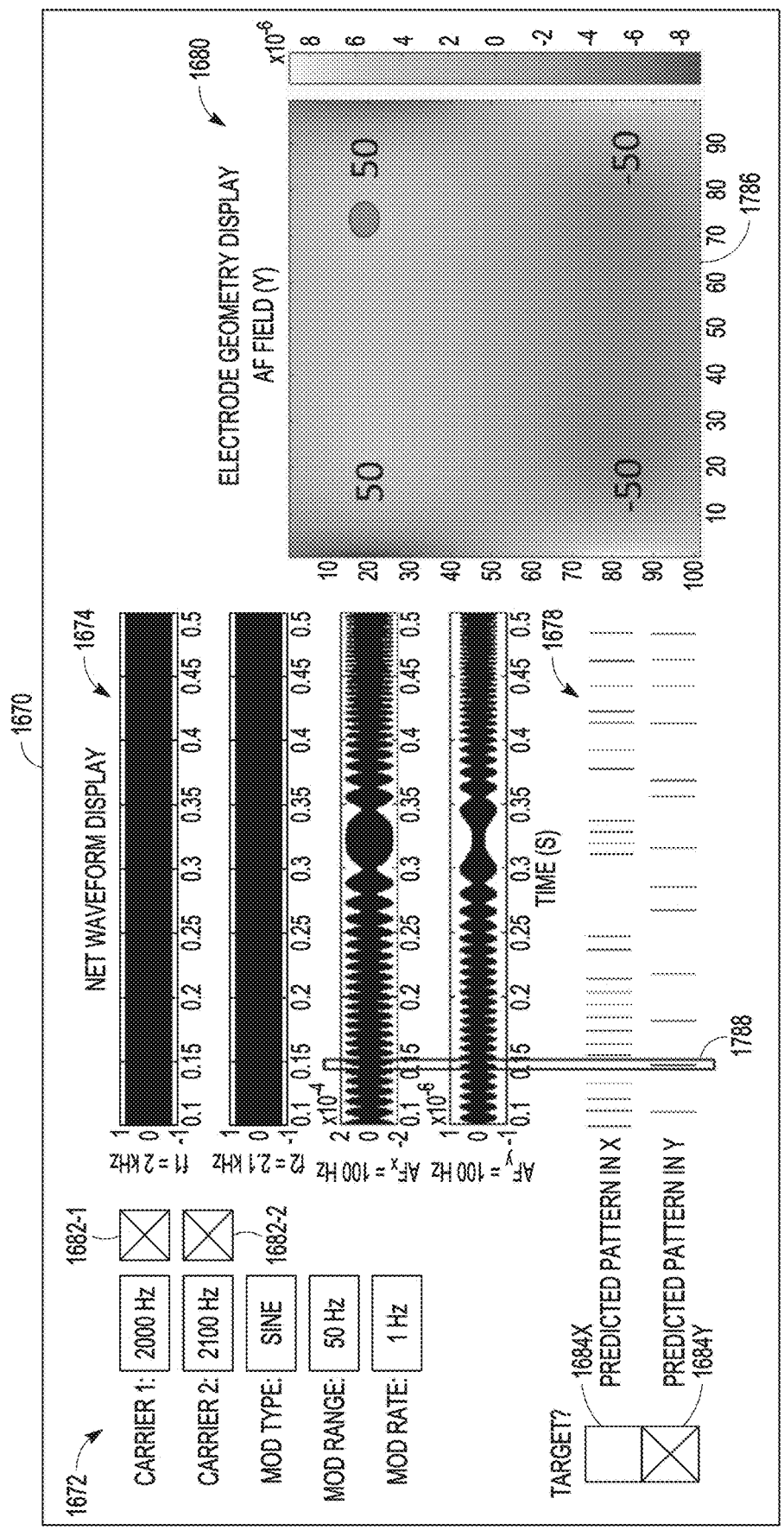
FIG. 17 illustrates the display screen of FIG. 16 showing an example of contents displayed for a specific point of time.
Figure 18:
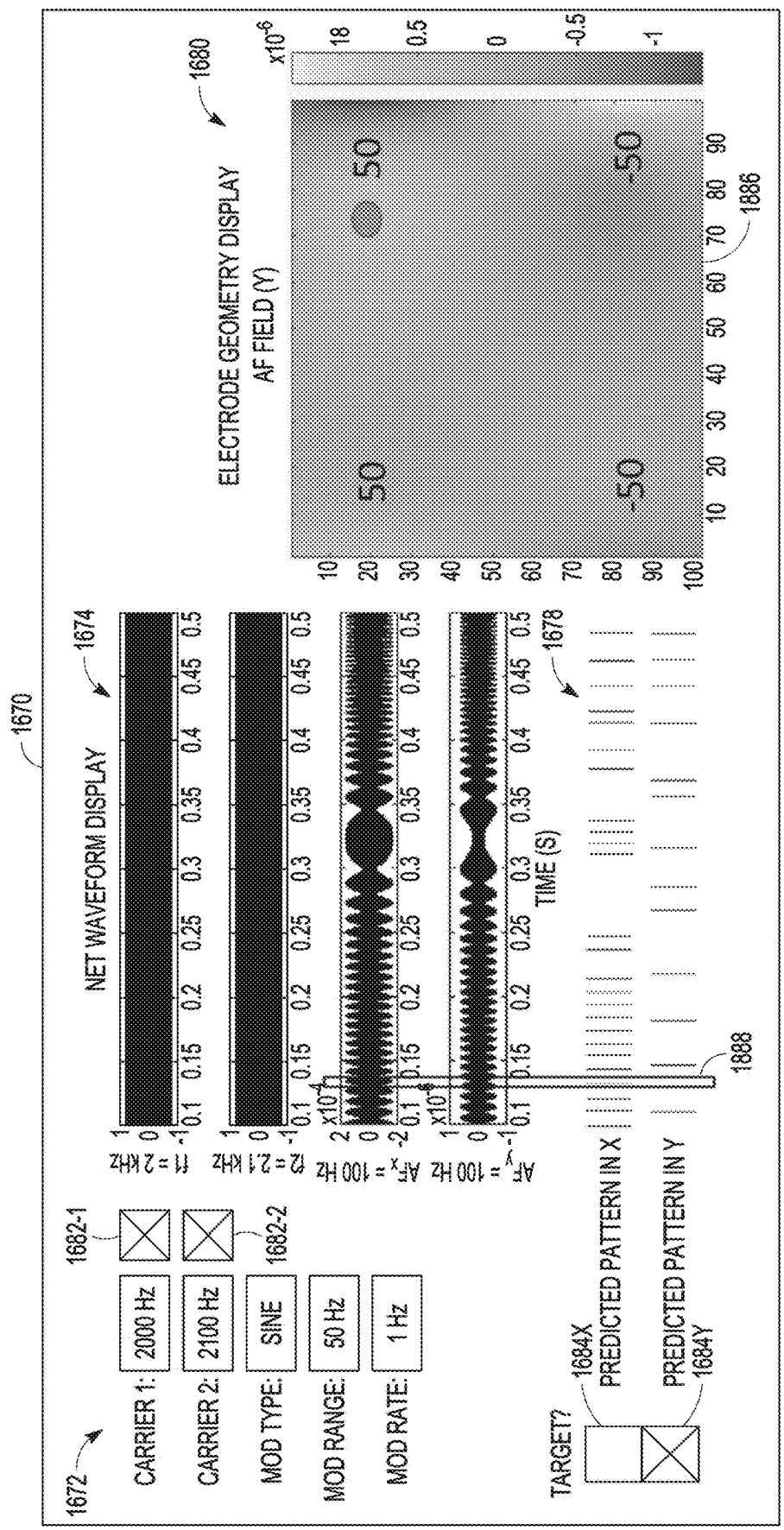
FIG. 18 illustrates the display screen of FIG. 16 showing an example of contents displayed for another specific point of time.

FIGS. 17 and 18 each illustrate display screen 1670 showing an example of contents displayed for a specific point of time. In FIG. 17, AF field 1786 showing $AF_Y$ is displayed for a time point 1788, when Y direction activation occurs.

In FIG. 18, AF field 1886 showing $AF_Y$ is displayed for a time point 1888, when Y direction activation does not occur. FIGS. 17 and 18 show that maxima in the AF change spatial locations across time according to interferential waveforms. In various embodiments, effects of waveform and field parameters in shape of stimulation fields and waveforms can be presented to the user using screen 1670 and/or calculated for back-end operations of programming device 1502 at specific time points.

Figure 19:
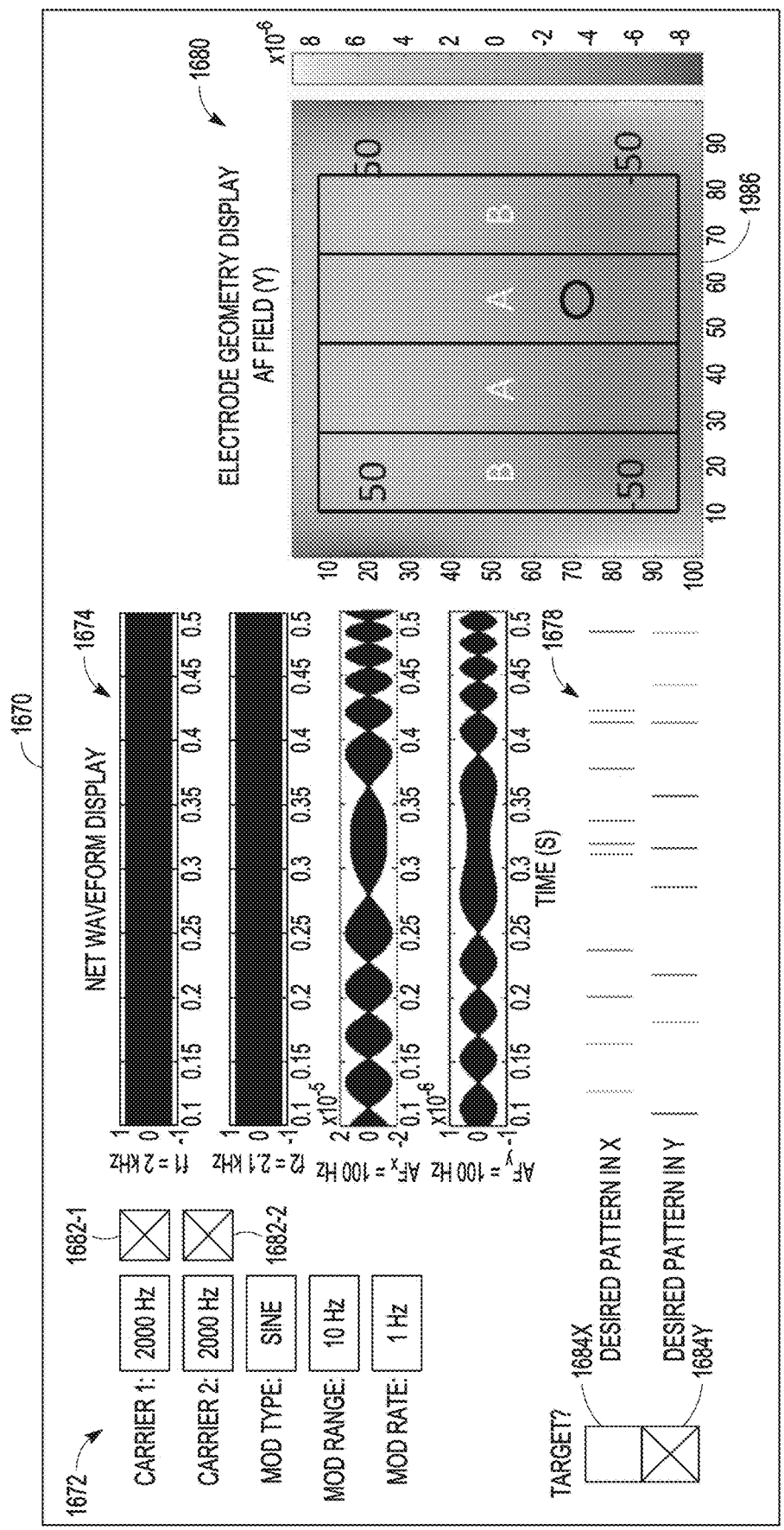
FIG. 19 illustrates an embodiment of providing recommendations as displayed on the display screen of FIG. 16.

FIG. 19 illustrates an embodiment of providing recommendations as displayed on screen 1670. In some embodiments, recommendations for generating desired asynchronous and/or non-regular patterns at desired locations can be provided to user based on apriori simulations, pre-loaded look up tables, and/or predictions such as those made by using AF models. The desired asynchronous and/or non-regular patterns of action potentials can be determined and displayed as desired patterns in net pattern display area 1678, and the corresponding temporal variation of the AF can be predicted (as displayed as, for example, AF field 1986 in Y direction), based on which the parameters defining the pattern of interferential stimulation can be determined for programming the stimulation device. In AF field 1986 as shown in FIG. 19, "A" represents region of interest through which first pattern is given, and "B" represents region of interest through which second pattern is given. Activation function field 1986 shows the desired patterns of the action potentials in X and Y directions for the first pattern ("A").

Figure 20:
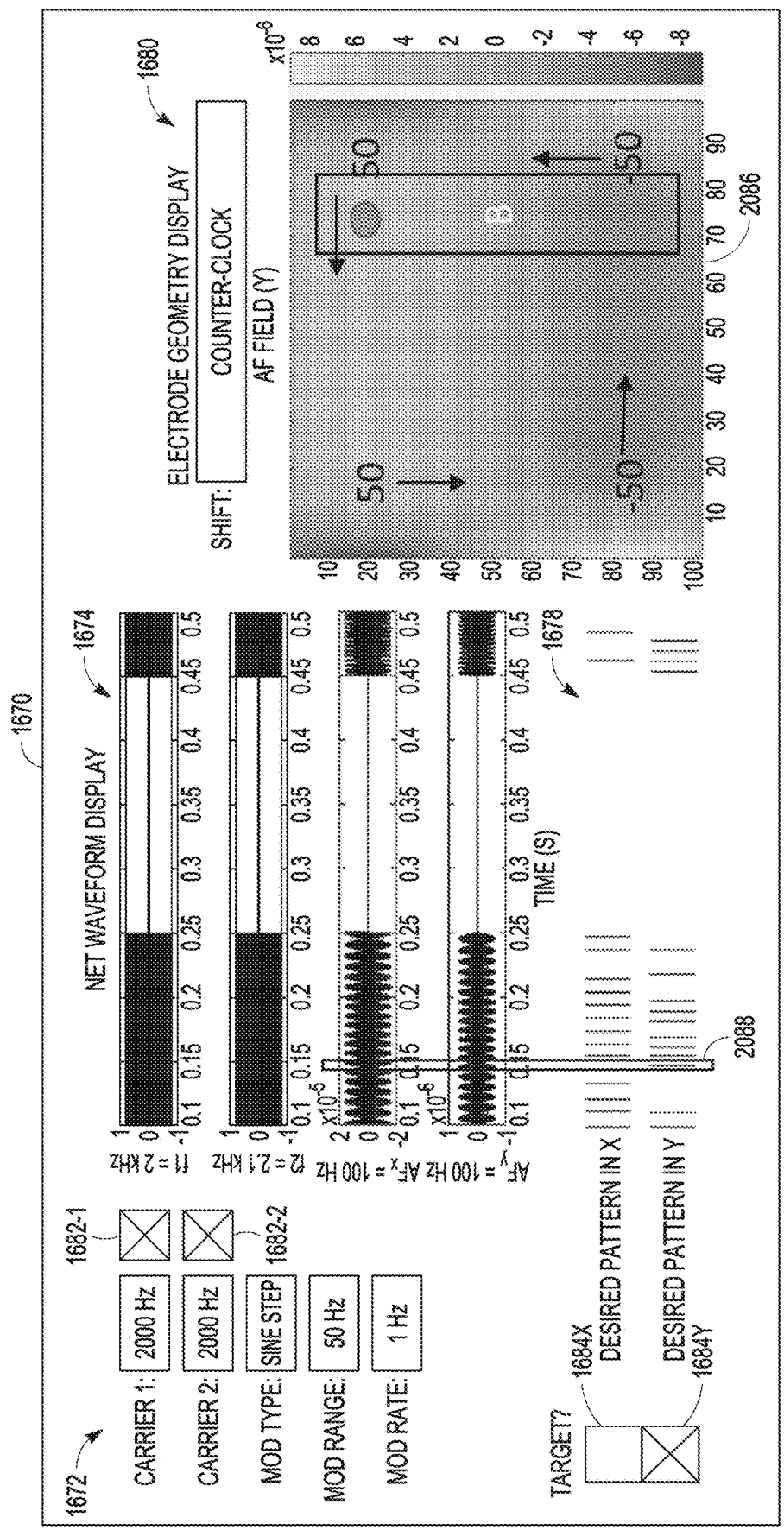
FIG. 20 illustrates an embodiment of using space-domain to modulate time-domain as displayed for a specific time on the display screen of FIG. 16.
Figure 21:
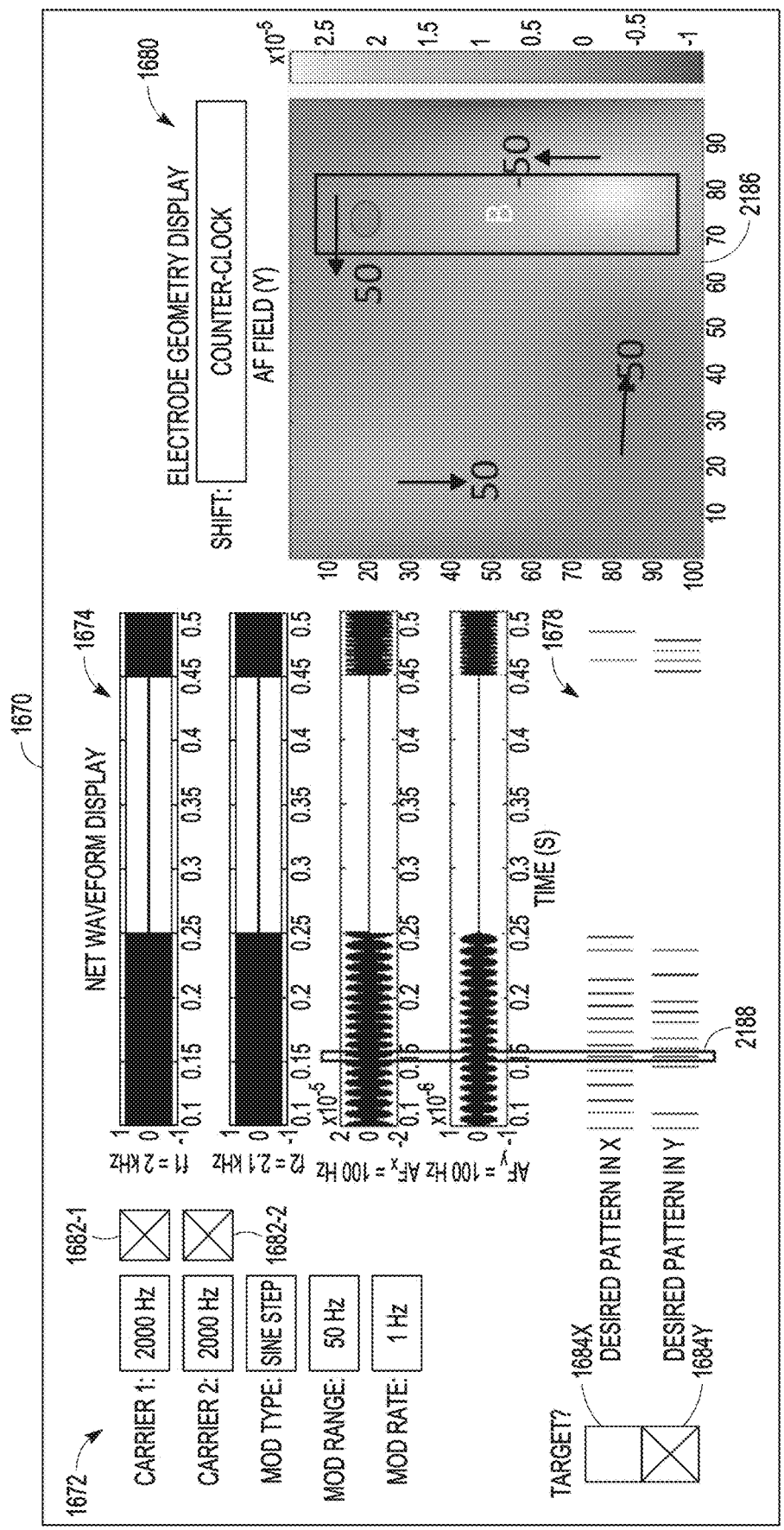
FIG. 21 illustrates an embodiment of using space-domain to modulate time-domain as displayed for another specific time on the display screen of FIG. 16.
Figure 22:
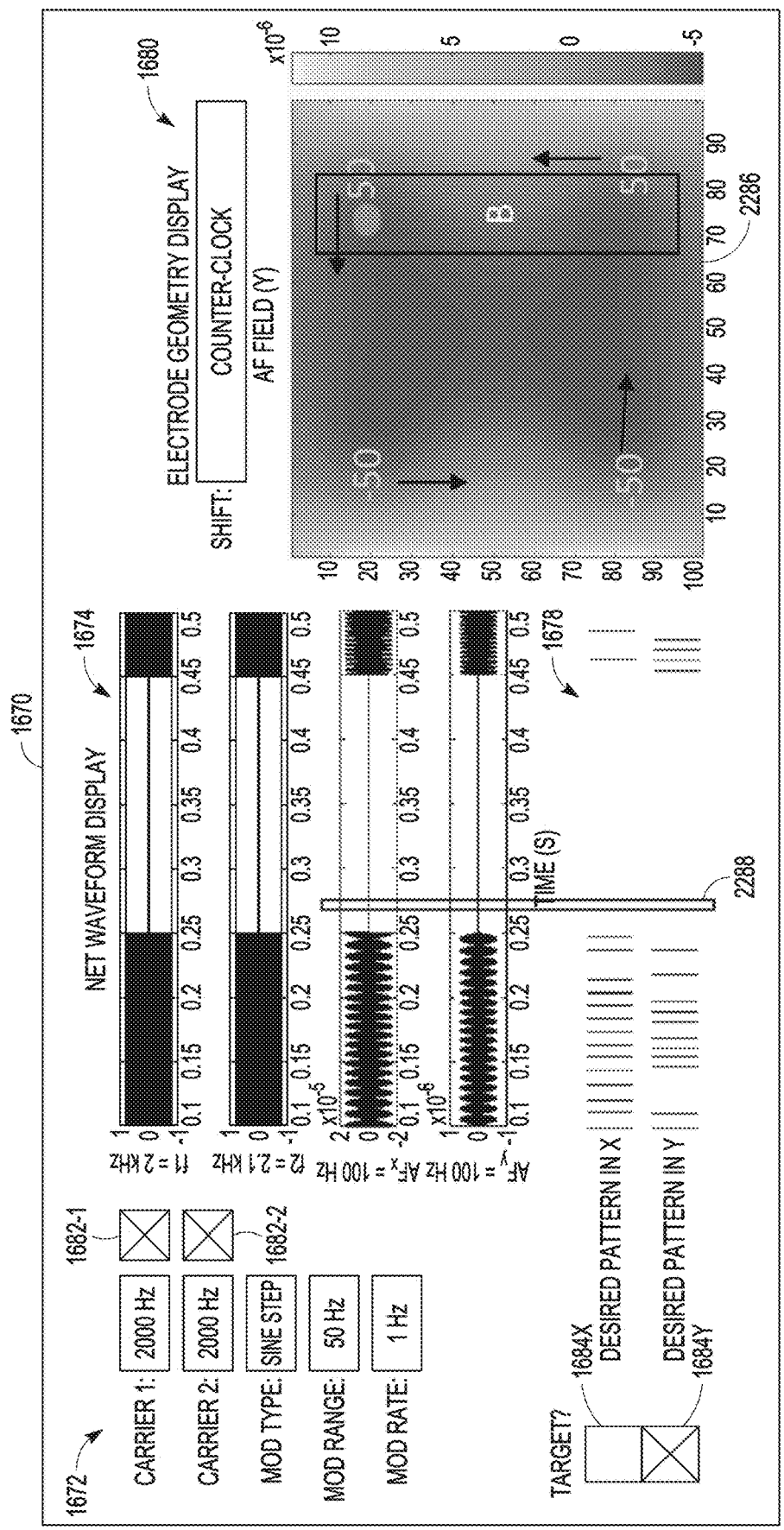
FIG. 22 illustrates an embodiment of using space-domain to modulate time-domain as displayed for another specific time on the display screen of FIG. 16.

FIGS. 20-22 each illustrate an embodiment of using space-domain to modulate time-domain as displayed for a specific time on screen 1670. In FIG. 20, AF field 2086 showing $AF_Y$ field is displayed for a time point 2088. In FIG. 21, AF field 2186 showing $AF_Y$ field is displayed for a time point 2188. In FIG. 22, AF field 2286 showing $AF_Y$ field is displayed for a time point 2288. FIGS. 20-22 show an example of the field parameters specified to be time-varying to modulate the beat frequency. This allows space-domain parameter changes (e.g., changes in the field parameters) to module the time-domain parameters (e.g., the waveform parameters). To enable spatial selectivity in the desired patterns and/or more time variation, the electrode geometry may be configured to "drift" in a pre-defined pattern (e.g., rotate counter-clockwise as illustrated in FIGS. 20-22) and/or to cycle on and off to prevent certain regions from activating. Neurons in denoted orientations activate at maxima of the AF for the corresponding direction. In FIG. 21, AF field 2186 as displayed changes with time showing the rotating field resulting from the rotating electrode geometry. In FIG. 22, AF field 2186 as displayed corresponds to a point of time when the stimulation amplitude is reduced (e.g., to zero), and/or when the activation field itself is generated to be non-conducive for activation.

Figure 23:
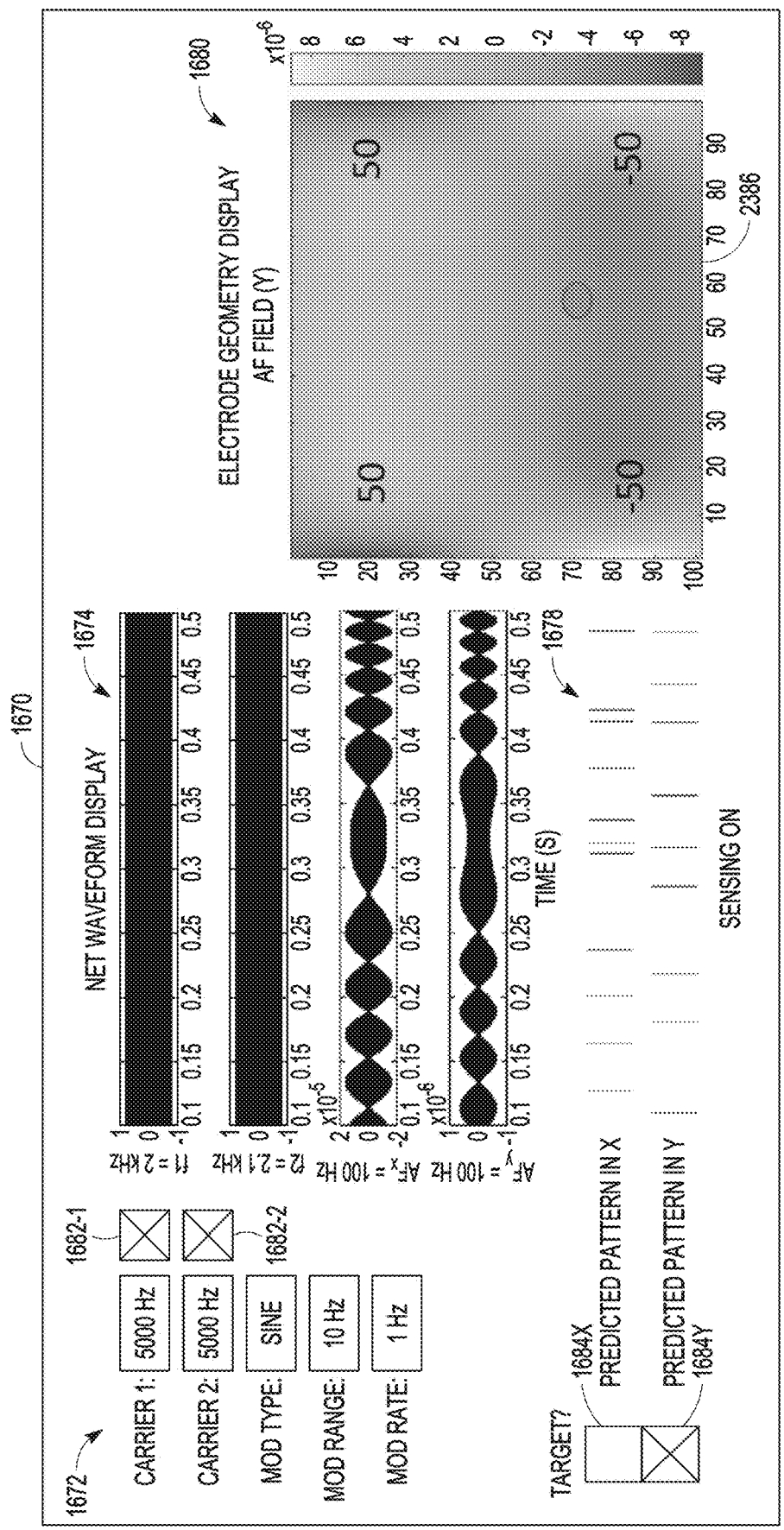
FIG. 23 illustrates an embodiment of integrating interferential stimulation with sensing capabilities as displayed on the display screen of FIG. 16.

FIG. 23 illustrates an embodiment of integrating interferential stimulation with sensing capabilities as displayed on screen 1670. Screen 1670 as shown in FIG. 23 indicates that sensing is on and an AF field 2386 is displayed. Sinusoidal waveforms used in the interferential stimulation is known to be more easily processed than rectangular stimulation waveforms. When sensing (e.g., electrospinogram) is required, the sinusoidal carrier waveforms having carrier frequency above a low pass cutoff frequency to minimize stimulation artifacts in the sensed signal. The modulation type can be fixed at "sine" (sinusoidal modulation type). The modulation range and/or the modulation rate can be fixed to prevent harmonics from contaminating sensed signal.

In various embodiments, the present subject matter provides a way to control delivery of neurostimulation for sub-perception pain relief. With properly configured waveforms and fields, asynchronous and/or non-regular interferential stimulation can enable time-varying spatial selectivity, the ability to by-pass specific tissue structures, and the ability to reach various specific targets (e.g., dorsal roots, lateral corticospinal tract, lateral reticulospinal tract, and lateral funiculus area). Waveforms being used in interferential stimulation (e.g., time-varying sinusoids) can have particular signal-generation and processing advantages (e.g. simpler function generator and/or use of simple filters) over other waveforms (e.g., rectangular pulses).

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation energy to target tissue including nerve fibers using a plurality of electrodes, the system comprising:
    a programming control circuit configured to generate stimulation parameters controlling the delivery of the neurostimulation energy according to a neurostimulation program including a pattern of interferential stimulation configured to effect at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration; and
    a user interface configured to determine the neurostimulation program and to provide the pattern of interferential stimulation with modulation of at least one of the first electrode configuration or the second electrode configuration to result in a time-varying modulated stimulation field and a time-varying modulated activation function having a beat frequency, the modulated stimulation field and the modulated activation function capable of effecting the at least one of asynchronous activation of the nerve fibers or non-regular activation of the nerve fibers, the beat frequency being a difference between the first and second frequencies.

2. The system of claim 1, wherein the user interface comprises:
    a presentation device configured to present user-programmable parameters and one or more effects of the user-programmable parameters in the pattern of interferential stimulation;
    a user input device configured to allow for editing of the pattern of interferential stimulation by adjusting the user-programmable parameters; and
    a stimulation control circuit configured to determine the neurostimulation program including parameters defining the pattern of interferential stimulation using the user-programmable parameters.

3. The system of claim 2, wherein the stimulation control circuit is further configured to determine waveform parameters of the parameters defining the pattern of interferential stimulation, the waveform parameters defining the first waveform and the second waveform.

4. The system of claim 3, wherein the stimulation control circuit is further configured to determine the waveform parameters including a first carrier frequency and a second carrier frequency for producing the first waveform using a first carrier waveform having the first carrier frequency and the second waveform using a second carrier waveform having the second carrier frequency.

5. The system of claim 4, wherein the stimulation control circuit is further configured to determine the waveform parameters for at least one of producing the first waveform by modulating the first carrier waveform or producing the second waveform by modulating the second carrier waveform.

6. The system of claim 5 wherein the stimulation control circuit is further configured to determine the waveform parameters for modulating at least one of the first carrier frequency or the second carrier frequency so that the at least one of the first career frequency or the second carrier frequency is time-varying.

7. The system of claim 6, wherein the stimulation control circuit is further configured to determine at least one of:
    a modulation range of the waveform parameters to be applied to the at least one of the first carrier frequency or the second carrier frequency, the modulation range being a range over which the at least one of the first carrier waveform or the second carrier waveform is modulated;

a modulation rate of the waveform parameters to be applied to the at least one of the first carrier frequency or the second carrier frequency, the modulation rate being a rate of change in time over which the at least one of the first carrier waveform or the second carrier waveform is modulated; or a modulation type specifying a manner in which the at least one of the first carrier waveform or the second carrier waveform is modulated.

8. The system of claim 2, wherein the stimulation control circuit is further configured to determine field parameters of the parameters defining the pattern of interferential stimulation, the field parameters defining the first electrode configuration and the second electrode configuration.

9. The system of claim 8, wherein the stimulation control circuit is further configured to determine the field parameters for making at least one of the first electrode configuration or the second electrode configuration time-varying.

10. The system of claim 9, wherein the stimulation control circuit is further configured to determine the field parameters to provide for an asymmetric stimulation field for focusing the delivery of the neurostimulation energy to a region of the target tissue, the region varying with the time-varying at least one of the first electrode configuration or the second electrode configuration.

11. A method for delivering neurostimulation energy to target tissue including nerve fibers using a plurality of electrodes, the method comprising:
   determining a pattern of interferential stimulation for effecting at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration and by modulating at least one of the first electrode configuration or the second electrode configuration to result in a time-varying modulated stimulation field and a time-varying modulated activation function having a beat frequency, the modulated stimulation field and the modulated activation function capable of effecting the at least one of asynchronous activation of the nerve fibers or non-regular activation of the nerve fibers, the beat frequency being a difference between the first and second frequencies;
   determining a neurostimulation program based on the determined pattern of interferential stimulation; and
   generating stimulation parameters for controlling the delivery of the neurostimulation energy according to the determined neurostimulation program.

12. The method of claim 11, further comprising:
   transmitting the generated stimulation parameters to an implantable stimulation device;
   delivering the neurostimulation energy from the implantable stimulation device; and
   controlling the delivery of the neurostimulation energy using the stimulation parameters received by the implantable stimulation device.

13. The method of claim 11, further comprising:
   presenting user-programmable parameters using a presentation device;
   presenting one or more effects of the user-programmable parameters in the pattern of interferential stimulation using the presentation device;
   allowing a user to edit the pattern of interferential stimulation by adjusting the user-programmable parameters based on the presented one or more effects; and
   determining parameters defining the pattern of interferential stimulation using the user-programmable parameters.

14. The method of claim 13, wherein determining the parameters defining the pattern of interferential stimulation comprises determining waveform parameters defining the first waveform and the second waveform, the waveform parameters including a first carrier frequency and a second carrier frequency for producing the first waveform using a first carrier waveform having the first carrier frequency and the second waveform using a second carrier waveform having the second carrier frequency.

15. The method of claim 14, wherein determining the waveform parameters further comprises determining the waveform parameters for at least one of producing the first waveform by modulating the first carrier waveform or producing the second waveform by modulating the second carrier waveform.

16. The method of claim 15, wherein determining the waveform parameters further comprises determining the waveform parameters for modulating at least one of the first carrier frequency or the second carrier frequency so that the at least one of the first career frequency or the second carrier frequency is time-varying.

17. The method of claim 16, wherein determining the waveform parameters further comprises at least one of
   determining a modulation range of the waveform parameters to be applied to the at least one of the first carrier frequency or the second carrier frequency, the modulation range being a range over which the at least one of the first carrier waveform or the second carrier waveform is modulated;
   determining a modulation rate of the waveform parameters to be applied to the at least one of the first carrier frequency or the second carrier frequency, the modulation rate being a rate of change in time over which the at least one of the first carrier waveform or the second carrier waveform is modulated; or
   a modulation type specifying a manner in which the at least one of the first carrier waveform or the second carrier waveform is modulated.

18. The method of claim 13, wherein determining the parameters defining the pattern of interferential stimulation comprises determining field parameters of the parameters defining the pattern of interferential stimulation, the field parameters defining the first electrode configuration and the second electrode configuration.

19. The method of claim 18, wherein determining the field parameters comprises determining the field parameters for making at least one of the first electrode configuration or the second electrode configuration time-varying.

20. A non-transitory computer-readable storage medium including instructions, which when executed by a system, cause the system to perform a method for delivering neurostimulation energy, the method comprising:
   determining a pattern of interferential stimulation for effecting at least one of asynchronous activation of the nerve fibers or non-regular activation of the nerve fibers by simultaneously delivering a first stimulation current having a first waveform with a first frequency to the target tissue using a first electrode configuration and a second stimulation current having a second waveform with a second frequency to the target tissue using a second electrode configuration and by modulating at least one of the first electrode configuration or the second electrode configuration to result in a time-varying modulated stimulation field and a time-varying modulated activation function having a beat frequency, the modulated stimulation field and the modulated activation function capable of effecting the at least one of asynchronous activation of the nerve fibers or non-regular activation of the nerve fibers, the beat frequency being a difference between the first and second frequencies;

determining a neurostimulation program based on the determined pattern of interferential stimulation; and generating stimulation parameters for controlling the delivery of the neurostimulation energy according to the determined neurostimulation program.

* * * * *